United States Patent [19]

Ohara

[11] 4,148,320
[45] Apr. 10, 1979

[54] ARTIFICIAL CARDIAC PACEMAKER

[75] Inventor: Yuichi Ohara, Tokyo, Japan

[73] Assignee: Kabushiki Kaisha Daini Seikosha, Japan

[21] Appl. No.: 760,979

[22] Filed: Jan. 21, 1977

Related U.S. Application Data

[63] Continuation of Ser. No. 556,164, Mar. 6, 1975, abandoned.

[51] Int. Cl.² ............................................. A61N 1/36
[52] U.S. Cl. ............................................. 128/419 PG
[58] Field of Search ................ 128/419 PG, 419 PT, 128/419 R, 421, 422, 423

[56] References Cited

U.S. PATENT DOCUMENTS

| 3,171,892 | 3/1965 | Pantle | 128/2.05 X |
| 3,638,656 | 2/1972 | Grandjean et al. | 128/419 PG X |
| 3,757,792 | 9/1973 | Mulier et al. | 128/419 PG |
| 3,920,024 | 11/1975 | Bowers | 128/419 PG |
| 3,949,758 | 4/1976 | Jirak | 128/419 PG |
| 3,985,142 | 10/1976 | Wickham | 128/419 PG |

Primary Examiner—William E. Kamm
Attorney, Agent, or Firm—Robert E. Burns; Emmanuel J. Lobato; Bruce L. Adams

[57] ABSTRACT

An artificial cardiac pacemaker for use with a heart comprises an output feedback preventing circuit for applying stimulating output pulses developed by the pacemaker to a heart while preventing the pulses from being fed back into the pacemaker and for detecting cardiac signals from the heart. A selective converter circuit is connected to the output feedback preventing circuit and functions to convert negative cardiac signals from the heart into positive signals and apply the signals to a low pass filter circuit which filters the signals to eliminate high frequency noise. A resettable circuit for the refractory period is connected to receive the filtered signals and establishes a predetermined refractory period after each QRS signal from the heart and provides a corresponding trigger signal to a delay circuit which responds thereto to provide a trigger pulse after a predetermined time delay. A generator circuit is connected to the delay circuit and responds to the trigger pulses to accordingly generate output pulse signals. An output stimulating circuit has an input connected to the generator circuit and an output connected to the output feedback preventing circuit and is driven by the pulse signals to produce corresponding stimulating output pulses suitable for heart stimulation.

6 Claims, 3 Drawing Figures

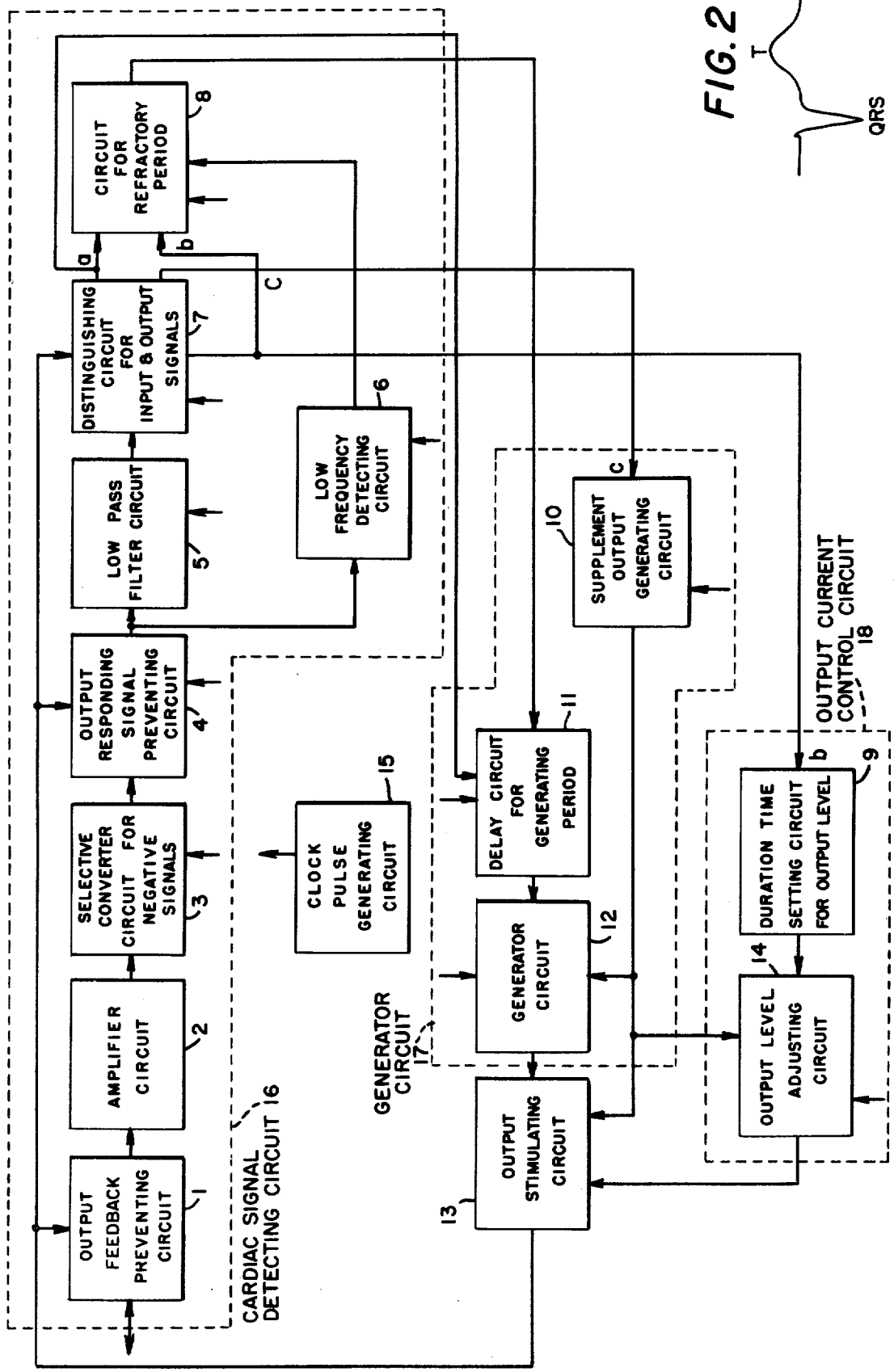

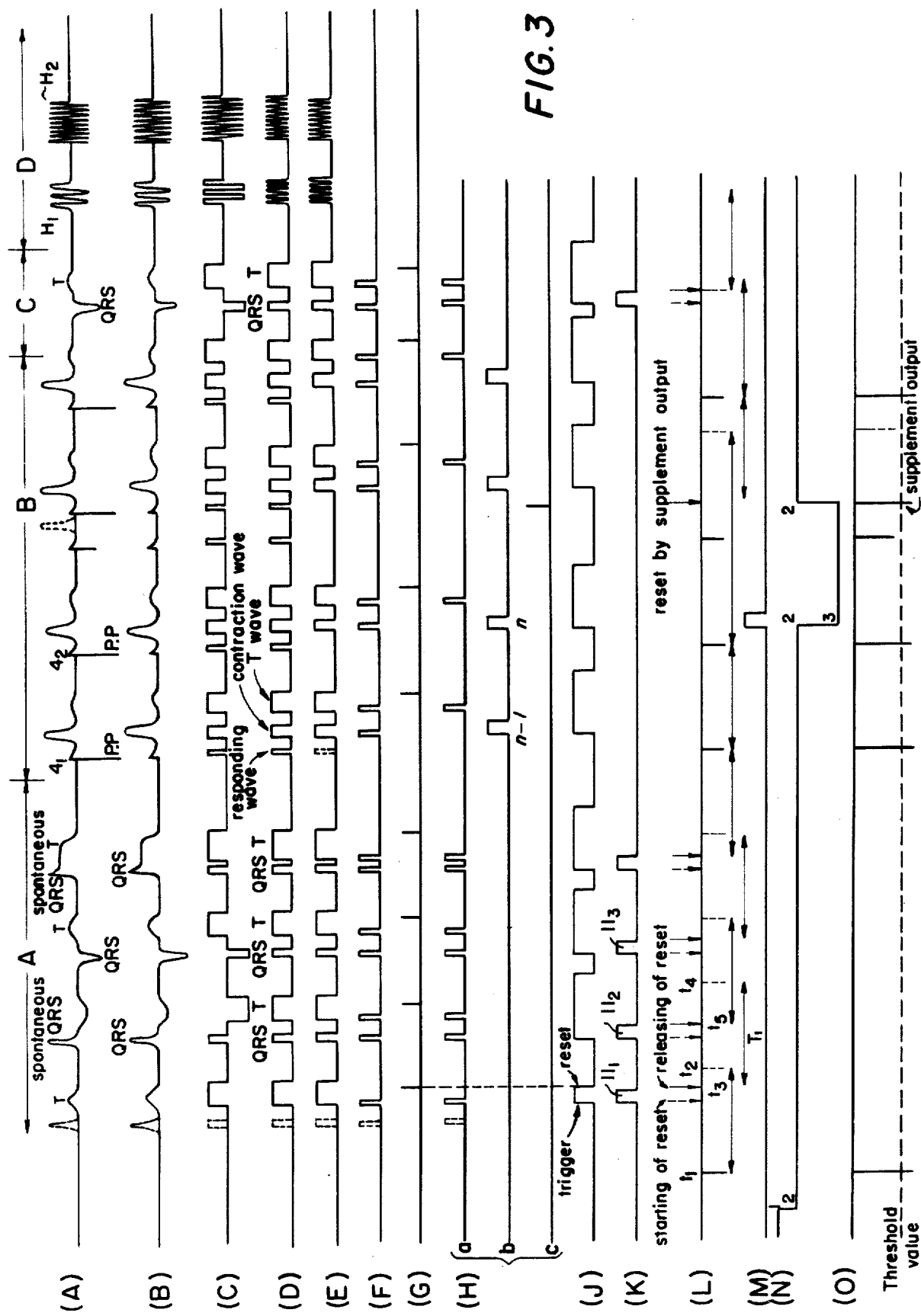

ARTIFICIAL CARDIAC PACEMAKER

RELATED APPLICATION

This application is a continuation of application Ser. No. 556,164 filed Mar. 6, 1975 and now abandoned.

BACKGROUND

This invention relates to an artificial cardiac pacemaker especially one in which the power consumption is extremely suppressed.

Most circuits in conventional artificial cardiac pacemakers are constructed from transistors, resistors and capacitors, wherein every operational function is secured by the combination of the elements.

This method requires, however, a rather long time and expense for inspecting the devices because the characteristics of each device, differ widely. Furthermore, the elements which define the circuit time constant, such as the generator and multivibrator, cannot be constructed without capacitors and resistors in addition to transistors.

Additionally, it is well know that capacitors are difficult to integrate and minimize by conventional fabrication techniques. The size of them is finitely limited, even though chip condensers are realized.

Cardiac pacemakers are known in which the stimulating current to the heart is decreased in a stepwise manner from a definite value to a threshold value at which the heart can firstly come to capture electrical cardiac signals and wherein such operations are cyclically repeated. In another application, the output level to the heart is determined by the value of a capacitor which is charged by paced QRS complex signals repeatedly caused by the output pulses. In this case, however, no stimulating pulse is given to the heart during the time between the last one pulse which is insufficient to be captured by the heart and the recovery to the former definite stimulating current, i.e., the time required for charging the capacitor. Thus the stimulation of the heart is extremely delayed. Moreover, rather higher capacitance should be available for discharging through the heart or reversely for fixing the stepdown intervals of stimulating current, and for holding the output level during the one pulse duration. As a result, capacitors should have higher capacitance and it is not yet possible to increase the capacitance without increasing the capacitor size and thus it is difficult to minaturize pacemakers utilizing such capacitors.

BRIEF SUMMARY OF THE INVENTION

For solving such problems, the apparatus according this invention comprises no capacitors, except in the clock pulse generating circuit, amplifier in the electrocardiac signal detecting circuit and output capacitor in and output circuit. Furthermore, these circuits are constructed as logic integrated circuits and therefore are small in size. In the inventive apparatus, the stimulating current is always fixed near the threshold value and when the current dips below the threshold value, supplement outputs are generated to rise up the stimulating current level so as to realize a pacemaker whose power consumption is suppressed as low as possible and simultaneously which supplies the required current to stimulate the heart and which can be constructed in a small size.

BRIEF DESCRIPTION OF THE DRAWINGS

FIG. 1 shows a block diagram of an embodiment of cardiac stimulating apparatus according to the present invention, FIG. 2 shows the waveform of typical cardiac signals given by the heart, and FIG. 3 shows signal waveforms which aid to understand the operations of the embodiment of the present invention.

DESCRIPTION OF PREFERRED EMBODIMENT

Referring now more particularly to the drawings, FIG. 1 shows a block diagram of one embodiment of apparatus according to the invention. In FIG. 1a feedback preventing circuit 1 is shown and which prevents the output from feeding back to the amplifier.

One of the input terminals of the said circuit 1 is connected to the heart, and picks up spontaneous electric signals from the heart (which are called hereinafter spontaneous signals) and the input terminal also receives electric signals generated by the output pulse for stimulating the heart through the said feedback preventing circuit 1 from an output stimulating circuit 13. In other words, the said circuit 1 receives two input signals, one of which occurs spontaneously and the other generated by the output pulse on the heart.

The said spontaneous signals and the said signals generated by the stimulation of output pulses are generally called the electrical cardiac potential of the heart (hereinafter, called the cardiac potential). Briefly explaining now as to spontaneous signal of the cardiac potential, the usual configuration of the spontaneous signals are shown in FIG. 2.

In FIG. 2, QRS means the QRS complex signals generated when the ventricle is contracted, and which is hereinafter called QRS complex as commonly called. On the other hand, T means the signals generated when the heart recovers, and which is hereinafter called T-wave.

In waveforms (A) of FIG. 3 the duration period A depicts spontaneous signals and the duration period B depicts signals generated by the stimulation by the output pulse.

The apparatus shown in FIG. 1 and its mode of operation will now be described with reference to the various waveforms depicted in FIG. 3. When output pulsess are derived from the output circuit 13, the output pulses are prevented from advancing to the amplifier 2 and downstream circuitry by the feedback preventing circuit 1. Therefore, pulses other than the said output pulses pass through the output feedback preventing circuit 1.

In waveform (B), the cardiac potential signals passing through the said circuit 1 are shown, and the cardiac signals are amplified in the amplifier circuit 2 which is of the saturation type. Accordingly, the cardiac signals amplified by the said amplifier 2 are transformed into rectangular waveforms at the output side of the amplifier 2, as shown by waveform (C).

The outputs of the amplifier 2 are passed to a selective converter 3 for converting only negative signals as input signals. Thus the signals amplified in the circuit 2 and transformed into rectangular waveforms are fed to the converter 3 and only negative signals of the said signals are converted as shown by waveform (D) so that only positive signals appear at the output of the circut 3.

When inverting the negative signals into positive signals, even successive positive and negative signals are separated one by one by clock pulses generated at the clock pulse generating circuit 15. As seen in FIG. 1, the clock pulse generating circuit 15 generates clock pulses which are represented by an output arrow and the clock pulses are applied to other circuits, such as the selective converter circuit 3, as represented by the input arrows applied to these circuits. For ease of presentation in the drawing and to avoid confusion, the lines interconnecting the generating circuit output to the other circuits has been omitted.

Output signals of the said selective converter circuit 3 for negative signals are led to the responding signal preventing circuit 4. In this circuit 4, responding signals $4_1, 4_2 \ldots 4_n$ (as shown in the period B of waveform (A)) which occur when an output capacitor (not shown) in the output circuit 13 is charged or discharged through the heart after output pulses applied to the heart are removed.

During the duration period A shown in waveform (A), however, no output pulses appear during the time that spontaneous signals of the heart are detected so that no responding signals against output pulses are present. Thus in this case, the said responding signal preventing circuit 4 is independent of responding signals against output pulses so that the circuit 4 advances signals from the said selective converter circuit 3 as shown by waveform (E).

Output branches of the responding signal preventing circuit 4 are connected respectively to a low pass filter circuit 5 and low frequency detecting circuit 6. Consequently, output signals from responding signal preventing circuit 4 shown by waveform (E) are applied to the low pass filter 5 and the low frequency detecting circuit 6.

In the said low pass filter 5, signals are filtered digitally by clock pulses and waves having a frequency component more than 50 Hz are removed. Thus, only QRS complex signals and T-waves are picked up as shown by waveform (F). Moreover, as shown in the period D of waveform (A), noises caused by induction noise H2 or internal hum $H_1$ from inputs of apparatus and additionally other high frequency signals (including one by induction) are removed.

Referring again to waveform (A), the duration period C depicts the restarting of spontaneous signals by the heart, in other words, spontaneous recovery duration, after that output pulses from the output circuit stimulate the heart when detecting the disappearance of spontaneous signals on the heart and consequently contracting waves of the heart are generated by this stimulating pulse as shown in the duration period B.

Now referring again FIG. 1, as above described, when the low pass filter 5 detects signals of the QRS complex and T-wave less than 50 Hz these low frequency, detected signals are sent to a distinguishing circuit 7.

On other hand, the said low frequency detecting circuit 6 counts clock pulses from the clock pulse generating circuit 15 and detects signals less than 4 Hz, such as signals of T-wave, etc., from signals delivered by the responsing signal preventing circuit 4, and accordingly develops acceptance signals at its output side.

The said acceptance signals are sent to the circuit 8 for refractory period, described below.

The signals passing through the said low pass filter 5 are applied to the said distinguishing circuit 7 as input signals, which also receives, as input signals output pulses from the output stimulating circuit 13 and clock signals from the clock pulse generating circuit 15. Thus by measuring periods by clock pulse signals, the circuit 7 distinguishes signals received from the filter 5 to be QRS compelx or T-wave signals or paced QRS complex signals caused by the systole by output pulse stimulation corresponding to output pulses from the output stimulating circuit 13. If the received signals are identified with spontaneous QRS complex or T-wave signals, the circuit 7 gives a signal "a" shown in waveform (H)a to the circuit 8 for refractory period and the dely circuit 11 for the generating period.

On the other hand, when the received signals are identified with the contraction potential caused by the stimulation with the output pulses, a signal "b" shown in waveform (H)b is given to the duration time setting circuit 9 for output level control and the circuit 8 for refractory period.

Furthermore during the duration period shown in waveform (A), when no contraction potentials by stimulating pulses are seen, even though output pulses stimulate the heart, the distinguishing circuit 7 detects the absence of contraction waves and provides signals shown in waveform (H)c to the supplement output generating circuit 10.

As shown described, signals "a" and "b" shown in waveforms (H) are applied to the circuit 8 for refractory period from the distinguishing circuit 7, and trigger the circuit 8 for refractory period. The signal "a" corresponds to spontaneous QRS complex and T-wave signals. When the circuit 8 is triggered by the signal corresponding to the T-wave signals, the circuit 8 is reset with the output signals from the low frequency detecting circuit 6 shown in waveform (G).

Waveform (J) shows the output signals of the said circuit 8 for the refractory period. As understood from the figure, the circuit 8 is immediately reset by the signal from the low frequency detecting circuit 6 and the circuit 8 is triggered by the signals corresponding to T-wave signals in signals "a" while the circuit 8 is not reset by the signals from the said detecting circuit 6 when the circuit 8 is triggered with signals corresponding to spontaneous QRS complex signals.

Thus in the circuit 8 for the refractory period, logical products, i.e. AND, etc. are derived from signals with a definite pulse width corresponding to spontaneous QRS complex signals and output signals from the low frequency detecting circuit 6, by signals "a" shown in waveform (H), so as to hold the output signals during the definite period. Thus the circuit 8 for refractory period comprises the refractory period to T-wave signal. Therefore referring now to waveform (J), the circuit 8 provides an output signal when signals corresponding to spontaneous QRS complex are received.

One of the output branches of the circuit 8 for refractory period is connected to the delay circuit 11, which is triggered only when output signals "a" from the distinguishing circuit 7 are recognized, as shown in waveform (K), when output signals from the circuit 8 are triggered as shown in waveform (J). Wherever the circuit 8 is reset, however, simultaneously the delay circuit 11 is reset. In other words, only signals triggering the circuit 8 with signals "a" of waveform (H) are transferred to the delay circuit 11 for generating period.

Signals shown in waveform (K) have a definite pulse width, and start to reset the generator 12 connected to the delay circuit 11 when rising (pulse leading edge), while the said signals release to reset when falling (pulse trailing edge).

Consequently, the generator circuit 12 starts to generate pulses with a period shown in waveform (L). Referring now to waveform (L), the generated output is arranged to appear at t2 after t1 if no signals are received by the generator 12 from the delay circuit 11. However, in the present illustration signals $11_1$ in waveform (K) are given from the delay circuit 11, so that the pulse generation is stopped, since the generator 12 is reset at pulse rising, as described above. Then when releasing of the reset of the generator 12 at pulse falling i.e. when the pulse generation is started, the generator 12 starts to generate pulses with the duration $T_1$. In other words, the delay circuit 11 gives signals $11_2$ to the generator 12 in the status shown in waveform (K), even though the generator is due to start pulse generation at the time $t_3$ in waveform (L) and then give output signals at the time $t_4$.

The generator 12 stops generating before the time $t_4$, i.e. at the pulse rising of signal $11_2$ shown in waveform (K), while starts to generate at the pulse falling of signals $11_2$, shown at the time $t_5$ in waveform (L). From here similarly the generator 12 is stopped at receiving the output signal from the delay circuit 11 and starts to generate pulses at every falling or sinking time of the signals generated by the delay circuit 11, as shown in waveform (K).

Consequently the generator 12 gives delayed signals at the first one pulse duration and thereafter generates further. The reason for the delay is to avoid the worse influences on heart, for example, to avoid competitive rhythm caused by more than one ordering system giving complex orders to the heart, when crossing the time when the heart occurs spontaneously QRS complex signals and the time when the stimulating output pulses stimulate the heart. So the delay circuit 11 gives signals delayed by the definite time from the specified time by the circuit 8 for the refractory period.

Now, in waveform (L), a dotted line means the time to give the next assumed generated signals, while a full line means the time when actually signals are given. Then, signals from the generator 12 are transferred to the stimulating output circuit 13 and drive the said circuit so as to give the stimulating output pulses to the heart from the circuit 13.

However, in the period A shown in waveform (A), the heart gives spontaneous signals, i.e., spontaneous QRS complex signals, and consequently no stimulating signals are given from the circuit 13. (see waveform (L)).

In the period B shown in waveform (A), no spontaneous QRS complex signals are given from the heart. Therefore, the stimulating output pulses are supplied from the circuit 13 through the feedback preventing circuit 1 and stimulate the heart.

The said stimulating output pulses are shown as P.P. in the period B in waveform (A). These stimulating pulses P.P. causes consequently the contraction potential and the recovery potential, as shown in waveform (A), since the heart is stimulated by the signal P.P.

The said contraction and recovery potentials are led to the circuit 1, which shows the identified waves at the output side and input side, as shown in waveform (B). The signals out of the said circuit are similarly transformed into the rectangular wave as shown in waveform (C) in the case of the period A, when passing through the amplifier 2.

Juat as same as in the case of A, only negative signals from the said amplifier 2 are converted into positive, and hereby, only positive signals are seen, as shown in waveform (D).

Output signals from the converter 3 for negative signals are given to the responding signal preventing circuit 4, whereby responding signals $4_1$, $4_2$, ... $4_n$ which occur during charging or discharging of the output capacitor in the circuit 13, are removed by counting of clock pulses from the clock pulse generating circuit 15. As a result, the responding signal preventing circuit 4 gives output signals shown in waveform (E).

From output signals of the said preventing circuit 4, signals corresponding only to the contraction and recovery potentials are picked up by the low pass filter 5, as shown in waveform (F) and transferred to the distinguishing circuit 7 for input signals. In the distinguishing circuit 7, the status is in the duration period B shown in waveform (A), wherein the signals corresponding only to the contraction and recovery potentials are given. In addition, only signals corresponding to the contraction waves are picked up shown as "b" in waveform (H) and transferred to the duration time setting circuit 9.

When "n" number of signals "b" shown in waveform (H) are given from this distinguishing circuit 7, pulse signals occur at the output side of the duration time setting circuit 9 as shown in waveform (M).

Behind the duration time setting circuit 9, the output level adjusting circuit 14 is connected. Accordingly, output signals of the said duration time setting circuit 9 are fed to the adjusting circuit 14.

Consequently, at the adjusting circuit 14, the output current goes down by one step width, as shown in waveform (N). More particularly, the output signal levels go down stepwise at every reception of outut signals from the duration time setting circuit 9.

Thus, the time depressing the output current of level adjusting circuit 14 is defined by the output from the duration time setting circuit 9. Since the output level adjusting circuit 14 is connected to the stimulating output circuit 13, the current levels of the stimulating pulses P.P. are stepwise depressed, every time the output signals of the level adjusting circuit 14 go stepwise down, as shown in waveform (N).

By the above described construction, one of the purposes of this invention to extend the battery lives, is satisfied. The power consumption and dissipation of the power source are decreased in comparison with the construction in which the definite level of output pulses P.P. is supplied from the circuit 13.

Morevoer, in the period B of waveform (A), when no contraction potentials are distinguished in the circuit 7, even though the stimulating pulses P.P. are given to the heart, for example, by the level down of the pulses P.P. at the above described case or the threshold value of the heart itself against the stimulation, the output signals of the circuit 7 are transferred to the supplement output generating circuit 10 as shown in "C" of waveform (H). The said generating circuit 10 is connected respectively to the generator 12, the stimulating output circuit 13, the output level adjusting circuit 14 and the duration time setting circuit 9.

Accordingly, when the output signals are given to the said generating circuit 10 from the distinguishing circuit 7, the generator 12 and the duration setting circuit 9 are reset by the output signal from the said supplement output generating circuit 10. Then the signals from the circuit 10 push up the output level of the adjusting circuit 14 by one step so as to drive the stimulating output circuit, and thereby the pulses P.P. are produced from the stimulating output circuit 13. Thus the level of the pulses P.P. are recovered as before, and the heart becomes able to capture the output pulses.

Thus it may be seen that the generation of the supplement output signals influences on the heart to stimulate the contraction from when the stimulation to the heart by pulses P.P. is given. But in the event no response is seen by the heart even after the raised level of the signals the supplement signals are, further raised up at one increment levels until the heart shows the response to the stimulation. However, when the stimulation signals are raised upto the maximum value, no supplement signals occur, until the reception of signals from the generator 12. Then if the heart recovers spontaneously, signals shown as in the period C in waveform (A) are given.

Roughly speaking, the operation in the period C is same as in the period A. Thus no description thereof is made to avoid repetition.

As to the construction of the invention, the feedback prevening circuit 1, the amplifier circuit 2, the selectively converting circuit 3 for negative signals, the output responding signal preventing circuit 4, the low pass filter circuit 5, the low frequency detecting circuit 6, the distinguishing circuit 7 for output signals and the circuit 8 for refractory period jointly comprise the cardiac signal detecting circuit 16. And further, the supplement output generating circuit 10, the delay circuit 11 for generating duration and the generator circuit 12 jointly compose the oscillating circuit 17, in a general sense. At last, the duration time setting circuit 9 for output level and the output level adjusting circuit 14 comprise the output current control circuit 18.

From the viewpoint of the wiring, the clock pulse generating circuit 15 is connected to the selective converting circuit 3 for negative signals, the output responding signal preventing circuit 4, the low pass filter circuit 5, the low frequency detecting circuit 6, the distinguishing circuit 7 for output signals, the circuit 8 for refractory period, the supplement output generating circuit 10, the delay circuit 11 for generating duration, the generator circuit 12 and the output level adjusting circuit 14.

As described above, this invention offers advantages in that it can be easily formed as integrated circuitry since no capacitors are involved except in the clock pulse generating circuit, the amplifier, the cardiac signal detecting circuit and the output capacitor in the output circuit. Also, the life of the electric cell can be prolonged since no output signals are developed when the heart generates apontaneously the QRS complex signals, while the output signals are given only when the absense of the cardiac spontaneous signals is seen detected and the output signals are adjusted in level.

Another advantage according to the invention, comprises the cardiac signal detecting circuit 16 which receives the standard signals of the clock pulse generating circuit 15 and selecting properly selects the time constant of the amplifier circuit 2 so as to distinguish the electrical cardiac potentials on the basis of the time standard in comparison with the usual means of selecting the cardiac potential by using frequency component as involved in the well-known artificial cardiac pacemaker. Especially, the above advantage is important, since it is difficult to find the characteristic frequency components for the cardiac potentials. In this case, the rising velocity and the pulse width of the said potential are available to pick up required signals.

Moreover, the circuitry according to this invention can consist of complementary MOS IC which require only small power consumption and dissipation, wherein the circuitry according to this invention can be easily constructed. Thus the life of the electric cell can consequently be prolonged and comact and small sized apparatus can be realized.

In addition, this invention comprises the supplement output circuit, so that the supplement output signal is immediately generated from the supplement output generating circuit to supply required current for stimulating the heart, even though the said stimulating output current comes out of the threshold value for stimulating the heart. Therefore delay of stimulation are nearly not seen independently of usual apparatus and the heart can be stimulated effectively with the minimum electric current for stimulation or which level is fixed always relatively and approximately. Thus a very highly reliable artificial cardiac pacemaker can be realized.

What we claim is:

1. An artificial cardiac pacemaker for use with a heart comprising: an output feedback preventing circuit for applying stimulating output pulses developed by the pacemaker to a heart while preventing said pulses from being fed back into the pacemaker and for detecting cardiac signals from the heart; a selective converter circuit connected to said output feedback preventing circuit and operative to convert negative cardiac signals from the heart into positive signals; a low pass filter circuit connected to said selective converter circuit for filtering the signals to eliminate high frequency noise; a resettable circuit for the refractory period connected to receive the filtered signals and operative to establish a predetermined refractory period after each QRS complex signal from the heart and provide a corresponding trigger signal; a delay circuit connected to receive the trigger signals are responsive thereto to provide a trigger pulse after a predetermined time delay; a generator circuit connected to said delay circuit and responsive to the trigger pulses to accordingly generate output pulse signals; an output stimulating circuit having an input connected to said generator circuit and an output connected to said output signal preventing circuit and being driven by the pulse signals to produce corresponding stimulating output pulses suitable for heart stimulation; a low frequency detecting circuit connected to receive the signals from said selective converter circuit and operative to detect therefrom signals below a predetermined frequency corresponding to T-wave signals and responsive to such detection to develop reset signals and apply the reset sinals to said resettable circuit to reset the same; and a clock pulse generating circuit for generating clock pulses for use as a time base and connected to apply said clock pulses to each of said selective converter circuit, low pass filter circuit, resettable circuit for the refractory period, generator circuit, low frequency detecting circuit, and delay circuit.

2. An artificial cardiac pacemaker according to claim 1, including a distinguishing circuit connected between said low pass filter and refractory period circuits and connected to receive the stimulating output pulses from said output stimulating circuit, said distinguishing circuit having means for developing a first output signal when it detects a paced QRS complex signal and developing a second output signal when no paced QRS complex signal is detected after the occurrence of a stimulating output pulse; and an output current control circuit connected to said distinguishing circuit for controlling the current level of said stimulating output pulses in response to said first or second output signals.

3. An artificial cardiac pacemaker according to claim 2; further comprising a supplement output generating circuit connected to said distinguishing circuit to receive therefrom said second output signal and responsive thereto to apply a signal to said output current control circuit to effect raising of the current level of said stimulating output pulses.

4. An artificial cardiac pacemaker according to claim 3; wherein said supplement output generating circuit includes means responsive to said second output signal to trigger said generator circuit into generating output pulse signals.

5. An artificial cardiac pacemaker according to claim 2; wherein said output current control circuit includes a duration time setting circuit operative to shift the level of said stimulating output pulses in a step-by-step manner is response to receipt of a predetermined number of said second output signals.

6. An artificial cardiac pacemaker according to claim 2; further including a low frequency detecting circuit connected to said selective converter circuit to receive the signals therefrom and operative to reset said resettable circuit for the refractory period in response to detection of low frequency noise in the cardiac signals.

* * * * *